United States Patent [19]

Quittmann

[11] Patent Number: 5,089,618

[45] Date of Patent: Feb. 18, 1992

[54] PROCESS FOR THE PURIFICATION OF ADENINE

[75] Inventor: Wilhelm Quittmann, Visp, Switzerland

[73] Assignee: Lonza Ltd., Gampel/Valais, Switzerland

[21] Appl. No.: 560,880

[22] Filed: Jul. 31, 1990

[30] Foreign Application Priority Data

Aug. 1, 1989 [CH] Switzerland ............ 2849/89

[51] Int. Cl.$^5$ ............ C07F 5/02; C07D 473/00
[52] U.S. Cl. ........................ 544/229; 544/277
[58] Field of Search .............. 544/224, 229, 277

[56] References Cited

FOREIGN PATENT DOCUMENTS 0045503 10/1982 European Pat. Off. ............ 544/224
2804723 2/1978 Fed. Rep. of Germany ...... 544/224
1518784 7/1978 United Kingdom ................ 544/224

OTHER PUBLICATIONS

Kirk–Othmer, Encycl. Chem. Tech., 3rd Ed., vol. 20, (1982) E. P. Pluedelemann, pp. 962 to 973.
C. A. Bruynes and T. K. Jurriens, J. Org. Chem., 47, (1982), pp. 3966 to 3969.

*Primary Examiner*—Mary C. Lee
*Assistant Examiner*—Robert C. Whittenbaugh
*Attorney, Agent, or Firm*—Fisher, Christen & Sabol

[57] ABSTRACT

Crude adenine, that is contaminated by 9-phenyladenine and/or colored additives, is converted with hexamethyldisilazane in the presence of a catalyst into N,N'-bis(trimethylsilyl) adenine, which is distilled and then reconverted into pure adenine by hydrolysis.

7 Claims, No Drawings

PROCESS FOR THE PURIFICATION OF ADENINE

BACKGROUND OF THE INVENTION

1. Field of the Invention

The invention relates to a process for the purification of adenine, especially of crude synthetic adenine, which optionally contains 9-phenyladenine and/or other byproducts.

2. Background Art

Adenine (6-aminopurine) plays an important role in nature as a component of nucleic acids, adenosine phosphates and other essential compounds. In addition to a direct pharmaceutical application ("vitamin $B_4$") and use in biochemical research, it is used, for example, as initial material for the production of pharmaceutical active ingredients (see, e.g., West Germany OS 2,804,723).

An important process for the production of adenine (European Published Patent Application No. 0,045,503; British Patent No. 1,518,784) starts from malonitrile, which is coupled with diazotized aniline to phenylazomalonitrile. The latter is reacted with ammonia and formamide to 4,6-diamino-5-phenylazopyrimidine which is cleaved reductively to 4,5,6-triaminopyrimidine and aniline. Adenine finally is obtained with formamide from the triaminopyrimidine. But the process takes place with the formation of by-products. As impurities, the crude adenine formed typically contains about 1 percent of 9-phenyladenine and about 2 to 5 percent of a brown substance of unknown constitution. To obtain a pure product with a content of over 99 percent, it previously was necessary to recrystallize the crude adenine, optionally in the form of the sulfate, using activated carbon several times. This type of purification is not only very tedious and time-consuming, but also causes considerable losses of substance; its yield is not over 75 percent.

BROAD DESCRIPTION OF THE INVENTION

The main object of the invention is to provide a purification process for such crude adenine that requires little labor and time and has small substance losses while at the same time achieving a high purity of product. Other objects and advantages of the invention are set out herein or are obvious herefrom to one skilled in the art.

The objects and advantages of the invention are achieved by the process of the invention.

The invention involves a process for the purification of crude adenine, which optionally contains 9-phenyladenine and/or other byproducts. The process includes converting the adenine into the N,N'-bis(trimethylsilyl) derivative, having the formula:

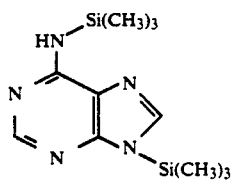

The adenine derivative is distilled in this form and then is reacted back into adenine again by solvolytic cleavage of the trimethylsilyl groups.

Preferably the conversion of the adenine takes place in the bis(trimethylsilyl) derivative with hexamethyldisilazane. Also preferably the conversion of the adenine in the bis(trimethylsilyl) derivative takes place in the presence of polyphosphoric acid and/or polyphosphoric acid trimethylsilylester as a catalyst. Preferably the solvolysis of the bis(trimethylsilyl) adenine takes place with water. Preferably the trimethylsilanol and/or hexamethyldisiloxane, as well as the optionally present organic solvents, resulting during the solvolysis of the bis(trimethylsilyl) adenine, are expelled by introducing water vapor.

DETAILED DESCRIPTION OF THE INVENTION

It was known that adenine can be converted into a distillable bis(trimethylsilyl) compound with silylation agents such as trimethylchlorosilane, a compound which with alcohol and/or water again yields adenine. Surprisingly, however, it was found that already in the case of a simple distillation over a column of slight separation efficiency (e.g., a Vigreux column of 30 cm length), not only the colored impurities but also the silylized 9-phenyladenine can practically completely be separated.

The conversion from adenine into the bis(trimethylsilyl) derivative is suitably performed with one of the known silylizing agents [see, e.g., E. P. Plueddemann in Kirk-Othmer, Encycl. Chem. Technol., 3rd Ed., Vol. 20, (1982), p. 962]. However, hexamethyldisilazane is preferred which in contrast with the otherwise frequently used chlorotrimethylsilane develops no hydrogen chloride but only ammonia as a byproduct. Ammonia escapes as a gas under the reaction conditions, while hydrogen chloride is bonded usually by triethylamine and must be removed by filtration as triethylammonium chloride. To perform the process on an industrial scale, it further is advantageous that no problems of corrosion occur in the use of hexamethyldisilazane and the distillation can take place directly from the reaction vessel of the silylation.

As catalysts for the silylation with hexamethyldisilazane, the usual catalysts, [see, e.g., C. A. Bruynes and T. K. Jurriens, J. Org. Chem., 47, (1982), page 3966], such as, concentrated sulfuric acid, saccharin or imidazole, can be used, especially preferred, however, are polyphosphoric acid or polyphosphoric acid trimethylsilylester. In comparison with the previously known silylation catalysts, these last-mentioned compounds are marked by low corrosiveness in combination with a volatility which can be disregarded, so that they remain completely in the residue in the distillation. The previously known silylation catalysts are either volatile themselves or they are silylized themselves, such as, the sulfuric acid, under the given reaction conditions, and thus form volatile byproducts which contaminate the distillate.

The distillation preferably is performed under reduced pressure in the order of magnitude of 10 mbars over a suitable column (e.g., a Vigreux column or a packed column) in which the receiver advantageously is heated to a temperature near the melting point (84° to 87° C.) of the bis(trimethylsilyl) adenine to avoid a solidification of the product.

The subsequent hydrolysis of the distillate can be performed directly with the melt; however, it also is optionally advantageous to dilute the distillate with a suitable inert solvent, such as, toluene.

The hydrolysis preferably takes place with hot water, and then preferably the resultant trimethylsilanol, which optionally is condensed partially or completely to hexamethyldisiloxane, as well as the optionally present solvent, are expelled with water vapor (vapor stripping). A preferred embodiment uses a large excess of water, which is distilled off until no more silanol or disiloxane passes over; especially preferred, however, is the use of a smaller amount of water, in which the silanol/disiloxane and optionally the solvent are expelled by introducing water vapor. The hexamethyldisiloxane optionally can be isolated from distilled-off mixture and can be used elsewhere; the trimethylchlorosilane or hexamethyldisilazane can be recovered from it using known processes and techniques. The latter then can optionally be used again in the first step of the process according to the invention, so that a closed circuit of the silylation agent results.

After cooling by centrifuging or filtration, the purified adenine can be isolated from the residue of the vapor stripping and, in the usual way, washed and dried.

The following examples illustrate the carrying out of the process according to the invention. Three different batches of crude adenine product (samples A, B and C) according to Table 1 were used as the initial material.

TABLE 1

| Sample | Content (HPLC, %) | | Transparency (%) |
| --- | --- | --- | --- |
| | Adenine | 9-Phenyladenine | |
| A | 94.5 | 0.2 | 2.1 (after filtration) |
| B | 91.5 | 1.1 | ≈0 (intensively brown) |
| C | 93.9 | 1.4 | 39.5 |

The content amounts of adenine and 9-phenyladenine, respectively, were determined by high pressure liquid chromatography (HPLC) on Nucleosil and UV detector. The transparency was measured, respectively, in hydrochloric acid solution (1 percent in 0.2n HCl) with light having a wavelength of 430 nm at a layer thickness of 1 cm.

EXAMPLE 1

In a 50 l agitator vessel of V4A steel, 13.5 kg of crude adenine product (sample A), 18.4 kg of hexamethyldisilazane and 10 ml of concentrated sulfuric acid were poured in at room temperature. The reaction mixture was refluxed with stirring until the completion of the development of the ammonia. After completion of the reaction, the excess silylation agent was distilled off at reduced pressure. The main product N,N'-bis(trimethylsilyl) adenine was distilled in a hot receiver by a small packed column at 4.5 torrs and a boiling temperature of 162° C. and then diluted under normal pressure with 20 l of toluene to avoid a crystallization of the distillate. For hydrolysis, 84.3 kg of a solution of silylated adenine in 34.6 kg of toluene (from 2 batches) was added in portions to 320 l of hot water of 75° to 80° C. In a slightly exothermal reaction, a large part of the volatile organic components (toluene, trimethylsilanol, hexamethyldisiloxane) was already distilled off during the addition. By outside heat input, additional water was distilled off in the mixture with the remainder of the volatile components. The end of the vapor stripping was achieved when a sample of the vapor condensate mixed with the same volume of semiconcentrated hydrochloric acid showed no more clouding. The suspended adenine was centrifuged after cooling to room temperature, washed with water and methanol and dried in a vacuum. After this procedure, 24 kg of adenine with a content of over 99.9 percent was obtained. Further analytical data is given in Table 3 below.

EXAMPLE 2

In a 250 ml glass round-bottom flask, 62.8 g of crude adenine product (sample A) was refluxed (8 to 10 hours) with 90.0 g of hexamethyldisilazane and 0.462 g of saccharin with exclusion of atmospheric moisture until completion of the development of the ammonia. The excess silylation agent was distilled off under vacuum. The silylated adenine was distilled over a Vigreux column (1 = 30 cm) at a pressure of 7 mbars and a head temperature up to 177° C. Thus, 117 g (95.4 percent) in N,N'-bis(trimethylsilyl)adenine was obtained. The distillate was dissolved in 90.2 g of toluene and fed into 440 ml of 75° hot water, and the volatile products of the hydrolysis together with the toluene were expelled with water vapor. The aqueous adenine suspension was cooled off at room temperature, filtered, washed with methanol and dried. Thus, 53.47 g (90.2 percent) of pure adenine was obtained. The analytical data of the product is also given in Table 3 below.

EXAMPLES 3 TO 7

According to the procedure of Example 2, different initial samples with various silylation catalysts were reacted, as shown in Table 2:

TABLE 2

| Example No. | Sample Designation | Catalyst | Yield % | Remarks |
| --- | --- | --- | --- | --- |
| 3 | B | Concentrated H$_2$SO$_4$ | 91.9 | |
| 4 | A | Polyphosphoric acid trimethylsilyl ester | 85.6 | Distillate as a melt hydrolyzed without toluene |
| 5 | A | Polyphosphoric acid | 86.6 | Distillate as a melt hydrolyzed without toluene |
| 6 | C | Saccharin | 96.7 | |
| 7 | A | Imidazole | 80.4 | Distillate as a melt hydrolyzed without toluene |

Note: The ratio of pure adenine obtained to the amount contained in the crude product was defined as yield.

TABLE 3

| Example No. | Results of Analyses | | Transparency (%) |
| --- | --- | --- | --- |
| | Content (HPLC, %) | | |
| | Adenine | 9-Phenyladenine | |
| 1 | >99.5 | <0.1 | 99.6–99.7 |
| 2 | 99.3 | <0.1 | 98.5 |
| 3 | 99.8 | <0.1 | 100.0 |
| 4 | 99.6 | <0.1 | 97.4 |
| 5 | 99.4 | <0.1 | 98.6 |
| 6 | 99.3 | <0.1 | 98.5 |
| 7 | 99.2 | <0.1 | 98.3 |

What is claimed is:

1. Process for the purification of crude adenine, which optionally contains 9-phenyladenine and/or other byproducts, consisting essentially of converting the adenine into the N,N'-bis(trimethylsilyl) derivative, having the formula:

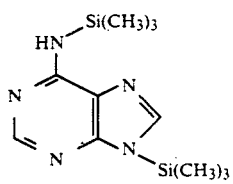

distilling the adenine derivative, and then reacting the adenine derivative back into adenine again by solvolytic cleavage of the trimethylsilyl groups, said solvolytic cleavage being effected by hydrolysis with water.

2. The process according to claim 1 wherein the conversion of the adenine takes place in the bis(trimethylsilyl) derivative with hexamethyldisilazane.

3. The process according to claim 2 wherein the conversion of the adenine in the bis(trimethylsilyl) derivative takes place in the presence of polyphosphoric acid and/or polyphosphoric acid trimethylsilylester as a catalyst.

4. The process according to claim 3 wherein the trimethylsilanol and/or hexamethyldisoloxane, as well as optionally present organic solvents, resulting during the solvolysis of the bis(trimethylsilyl) adenine, are expelled by introducing water vapor.

5. The process according to claim 1 wherein the trimethylsilanol and/or hexamethyldisiloxane, as well as optionally present organic solvents, resulting during the solvolysis of the bis(trimethylsilyl) adenine, are expelled by introducing water vapor.

6. The process according to claim 1 wherein the water used in the solvolysis is hot water.

7. The process according to claim 4 wherein the water used in the solvolysis is hot water.

* * * * *